US006501827B1

(12) United States Patent
Takasawa

(10) Patent No.: US 6,501,827 B1
(45) Date of Patent: Dec. 31, 2002

(54) EXAMINATION SYSTEM, IMAGE PROCESSING APPARATUS AND METHOD, MEDIUM, AND X-RAY PHOTOGRAPHIC SYSTEM

(75) Inventor: Toru Takasawa, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/407,086

(22) Filed: Sep. 28, 1999

(30) Foreign Application Priority Data

Sep. 29, 1998 (JP) ............................................ 10-275231

(51) Int. Cl.⁷ .............................................. G06F 19/00
(52) U.S. Cl. ........................ 378/116; 378/98.2; 378/62
(58) Field of Search ................................ 378/116, 165, 378/162, 210, 62, 98.2, 98.5

(56) References Cited

U.S. PATENT DOCUMENTS 4,774,720 A * 9/1988 Carbon ........................ 378/116
5,440,607 A * 8/1995 Nakaya ....................... 378/116

* cited by examiner

Primary Examiner—Drew A. Dunn
(74) Attorney, Agent, or Firm—Fitzpatrick, Cella, Harper & Scinto

(57) ABSTRACT

In order to improve ease of operation in an X-ray photographic system for performing X-ray photography (radiography) for taking a plurality of photographs (radiographs) when a photographic request is received from an external source; when photographs of a plurality of regions are to be taken, an examination system includes a device for changing the input photographic sequence of the regions to be photographed, a device for taking photographs in accordance with the changed photographic sequence, and a device for outputting the photographed results in a desired sequence.

42 Claims, 12 Drawing Sheets

FIG. 2A

| EXAMINATION ID | PATIENT ID | NAME OF PATIENT | PHYSIQUE | SEX | | |
|---|---|---|---|---|---|---|
| 00000001 | 123456789 | TARO YAMADA | NORMAL | MALE | CERVICAL VERTEBRAE A→P<br>RADIOGRAPHING REQUEST OBJECT ID 10021<br>RADIOGRAPHING CONDITIONS<br>72kV 160mA 56msec 120cm<br>IMAGE PROCESSING PARAMETER<br>Img.Process=D1, 3.0; C10: L5 | CERVICAL VERTEBRA FORAMEN<br>RADIOGRAPHING REQUEST OBJECT ID 10024<br>RADIOGRAPHING CONDITIONS<br>72kV 160mA 56msec 50cm<br>IMAGE PROCESSING PARAMETER<br>Img.Process=D1, 3.0; C10: L5 |

{ PATIENT INFORMATION } { INFORMATION INDICATING RADIOGRAPHING CONTENTS }

RADIOGRAPHING REQUEST OBJECT

FIG. 2B

| EXAMINATION ID | PATIENT ID | NAME OF PATIENT | PHYSIQUE | SEX | |
|---|---|---|---|---|---|
| 00000001 | 123456789 | TARO YAMADA | NORMAL | MALE | CERVICAL VERTEBRA IN FOUR DIRECTIONS<br>RADIOGRAPHING REQUEST OBJECT ID 11000 |

{ PATIENT INFORMATION } { INFORMATION INDICATING RADIOGRAPHING CONTENTS }

RADIOGRAPHING REQUEST MENU

| RADIOGRPHING ORDER NAME | ORDER OF REQUEST SOURCE | ORDER OF TECHNICIAN A | ORDER OF TECHNICIAN B | SERVER SHARED IN SURGERY | SERVER SHARED IN INTERNAL MEDICINE |
|---|---|---|---|---|---|
| SURGEON A THORACIC VERTEBRA IN FOUR DIRECTIONS | CERVICAL VERTEBRA FRONT → CERVICAL VERTEBRA FORAMEN → CERVICAL VERTEBRA SIDE → CERVICAL VERTEBRA RIGHT REAR OBLIQUE REGION | CERVICAL VERTEBRA FRONT → CERVICAL VERTEBRA SIDE → CERVICAL VERTEBRA RIGHT REAR OBLIQUE REGION → CERVICAL VERTEBRA FORAMEN | CERVICAL VERTEBRA FORAMEN → CERVICAL VERTEBRA FRONT → CERVICAL VERTEBRA SIDE → CERVICAL VERTEBRA RIGHT REAR OBLIQUE REGION | CERVICAL VERTEBRA FRONT → CERVICAL VERTEBRA SIDE → CERVICAL VERTEBRA FORAMEN → CERVICAL VERTEBRA RIGHT REAR OBLIQUE REGION | NOT SENT |
| SURGEON B THORACIC VERTEBRA IN FOUR DIRECTIONS | CERVICAL VERTEBRA FRONT → CERVICAL VERTEBRA FORAMEN → CERVICAL VERTEBRA SIDE → CERVICAL VERTEBRA RIGHT REAR OBLIQUE REGION | CERVICAL VERTEBRA FRONT → CERVICAL VERTEBRA SIDE → CERVICAL VERTEBRA RIGHT REAR OBLIQUE REGION → CERVICAL VERTEBRA FORAMEN | | | |
| PHYSICIAN A THORACIC VERTEBRA IN FOUR DIRECTIONS | CERVICAL VERTEBRA FRONT → CERVICAL VERTEBRA SIDE → CERVICAL VERTEBRA ANTEFLEXION → CERVICAL VERTEBRA RETROFLEXION | CERVICAL VERTEBRA FRONT → CERVICAL VERTEBRA ANTEFLEXION → CERVICAL VERTEBRA RETROFLEXION → CERVICAL VERTEBRA SIDE | CERVICAL VERTEBRA SIDE → CERVICAL VERTEBRA FRONT → CERVICAL VERTEBRA ANTEFLEXION → CERVICAL VERTEBRA RETROFLEXION | NOT SENT | CERVICAL VERTEBRA FRONT → CERVICAL VERTEBRA SIDE → CERVICAL VERTEBRA ANTEFLEXION → CERVICAL VERTEBRA RETROFLEXION |
| PHYSICIAN B THORACIC VERTEBRA IN FOUR DIRECTIONS | ... | CERVICAL VERTEBRA SIDE | | | |

FIG. 10

EXAMINATION SYSTEM, IMAGE PROCESSING APPARATUS AND METHOD, MEDIUM, AND X-RAY PHOTOGRAPHIC SYSTEM

BACKGROUND OF THE INVENTION

1. Field of the Invention

The present invention relates to an examination system suitable for an X-ray photographic system, for example, for taking an order from a doctor for the taking of an X-ray photograph (radiograph) and for performing X-ray photography (radiography), to an image processing apparatus and method, and to a medium therefore.

2. Description of the Related Art

An "X-ray photographic apparatus" refers to an apparatus for detecting X-rays, which have been transmitted through a patient, to form an image. This image is formed by representing differences in the transmittance of each type of the tissue structure in the body of the patient and the thickness thereof as a photographic density. It is important for a good X-ray image that as much information as possible be displayed in a readily visible manner. The position of the patient, the direction of X-ray irradiation, photographic conditions, etc., exert large influences thereon. Accordingly, when a doctor orders an X-ray photograph be taken, X-ray information such as the area to be X-rayed, the X-raying directions, the X-raying methods, etc., is typically specified together with patient information such as the name and the ID number of the patient. The information is then sent to a technician, and the X-raying is performed. If a plurality of X-ray photographs are to be taken, X-ray photographic request information, together with the patient information such as the name and the ID number of the patient, is included in the X-ray photograph order, for example, "chest portion A→P," "chest portion R→L," "cervical vertebra R→L," or "cervical vertebra A→P."

FIG. 12 shows an X-ray photographic system in which an X-ray photographic apparatus and an X-ray generation apparatus are combined, which shows an example contrasted to the present invention. In FIG. 12, reference numeral 100 denotes an X-ray tube for emitting X-rays. Reference numeral 101 denotes an X-ray generation apparatus. Reference numeral 102 denotes an operation and display section of the X-ray generation apparatus, for performing operation of the X-ray generation apparatus. These are usually collectively termed an "X-ray generation apparatus". On the other hand, the X-ray photographic apparatus comprises a standing position sensor unit 103 capable of performing X-ray photography of a patient in a standing position, a recumbent position sensor 105, an X-ray photographic system control section 107 for controlling this sensor, and an operation and display section 108 of the X-ray photographic system. Also, reference numeral 104 denotes a standing position sensor panel, and reference numeral 106 denotes a recumbent position sensor panel. The electrical charge corresponding to the amount of transmitted X-rays, detected by the standing position sensor panel 104 and the recumbent position sensor panel 106, is converted from analog into digital form and is input as an electronic image to the X-ray photographic system control section 107. Also, reference numeral 110 denotes a network which is connected to an imager 111.

When patient reception has been completed, a patient proceeds to a section of a corresponding examination department (for example, brain surgery, internal medicine, surgery, orthopedic surgery, etc.), and the patient's illness is diagnosed. For example, there are cases in which, in order to examine cervical vertebrae in a surgery department, it is desirable to see X-ray images of cervical vertebrae taken from four different directions. Examples of the four directions of the cervical vertebrae include "cervical vertebrae, front," "cervical vertebrae, foramen," "cervical vertebrae, side," and "cervical vertebrae, right rear oblique region."

The "cervical vertebrae, front" is obtained by a method in which the X-ray photograph is taken when the patient is made to stand facing the X-ray generation apparatus Adjustments are made so that the forehead is horizontal to the standing position sensor panel 104, and the angle and position of the X-ray tube 100 are adjusted so that X-rays can be emitted toward the fourth cervical vertebra of the patient. In a method for properly positioning the "cervical vertebrae, foramen," the patient is made to lie supine on the recumbent position sensor unit 105, the mouth is opened to the fullest, the line connecting the head in the median plane to the external ear foramen and the line connecting the base of the nose to the external ear foramen are made perpendicular to each other, and the X-ray tube is set to be perpendicular to the recumbent position sensor panel 106 so that the radiation focus is at the head in the median plane. In a method for properly positioning the "cervical vertebrae, side," the patient is made to stand facing 90 degrees away from the standing position sensor unit 103, the jaw is made to project forward slightly, the shoulders are made to lower, and the X-ray focus becomes incident on the fourth cervical vertebra. In a method for properly positioning the "cervical vertebra, right rear oblique region," the standing position sensor panel 104 and the patient form an angle of 50°, with the shoulder being the center; then, the jaw is made to project forward slightly, and the shoulders are made to lower.

A doctor writes the order for the X-ray photographing of the cervical vertebra in four directions on a radiology record card. At this time, the photographing order is written in the order in which the doctor wishes to subsequently view the images. For example, the order may be "cervical vertebra, front"→"cervical vertebra, foramen"→"cervical vertebra, side"→"cervical vertebra, right rear oblique region." Alternatively, there are cases in which the photographing order is indicated by "cervical vertebra, four directions." At this time, the meanings indicated by "cervical vertebra, four directions" may differ depending on the examination department (i.e., in the brain surgery department, "cervical vertebra, front"→"cervical vertebra, side"→"cervical vertebra, anteflexion"→"cervical vertebra, retroflexion"), the sequence may differ from doctor to doctor, and the sequence may differ depending upon the facilities.

The patient, with this radiology record card in hand, proceeds to the radiotherapy department and submits it to the receptionist. When it is the patient's turn to be X-rayed, the patient is taken to a room in which the X-ray photographic system in FIG. 12 is disposed. The technician first examines the patient information such as the ID number and the name written on the radiology record card, confirms the identity of the patient and then inputs this data by using the operation and display section 108. This data is required to confirm a match between the images and the patient and to assist the doctor in interpreting the images. Next, after the technician reads the X-ray photography order written on the radiology record card, the patient is correctly positioned; at the operation console 102 of the X-ray generation apparatus, the tube voltage, the tube current, and the irradiation time or the photo-timer are set; and in the operation console 108 of the X-ray photographic apparatus, image processing parameters, the imager 111 of the transfer destination, etc., are set to perform X-ray photography.

First, a case is described in which X-ray photography is conducted in the order as written on the radiology record card. The technician, after reviewing the radiology record card, performs X-ray photography of the "cervical vertebra, front." The patient is made to stand facing the X-ray generation apparatus, and adjustments are made so that the forehead is parallel to the standing position sensor panel 104. Also, the angle and position of the X-ray tube 100 are adjusted so that X rays can be omitted toward the fourth cervical vertebra of the patient. At this time, the position of the X-ray tube 100 is such that X-rays are emitted toward the fourth cervical vertebra of the patient from 15° below the fourth cervical vertebra. Examples of the X-ray photographic conditions are as follows: the distance between the standing position sensor panel 104 and the X-ray tube 100 is 120 cm, the tube voltage of the X-ray tube 100 is 72 kV, the tube current is 160 mA, the irradiation time is 56 msec, and the cross grid and the tube are focused on a small area. After the photographic preparations are completed and photography is possible, the irradiation switch in the vicinity of the operation and display section 102 ot the X-ray generation apparatus is pressed, and X rays are emitted from the X-ray tube 100 to the standing position sensor unit 103. X-rays emitted from the X-ray tube 100 pass through the patient and are converted into electricity of various amounts by the standing position sensor panel 104. This electricity is then amplified by an amplifier, signal processing, such as analog/digital conversion, is performed thereon, and the result is obtained as a digital image. The image input to the control section 107 of the X-ray photographic system is subjected to various image processings, such as gradation processing or highlight processing, and is displayed on the operation and display section 108 of the X-ray photographic system. The technician examines the image, and if it is necessary to retake the X-ray photograph, a rephotographing key is then pressed to retake the image. If it is not necessary to retake the X-ray photograph, then the technician performs second and subsequent X-ray photography in a similar manner.

X-ray photography is then performed for "cervical vertebra, foramen." "cervical vertebra, side," and "cervical vertebra, right rear oblique region." When the photography of the "cervical vertebra, four directions" is completed, the termination key is pressed to transfer the four obtained images to the imager 111 via the network 110 so that the images are displayed on film, and these images are passed on to the doctor for examination. However, since the X-ray photography of the "cervical vertebra, foramen" for the second photography is performed by the photographic apparatus with the patient in a recumbent position, the proper positioning of the patient is time-consuming, causing problems in that this is burdensome and the rate at which X-rays may be taken is low.

Next, a case is described in which the X-ray photographic technician performs X-ray photography in a sequence in which it is easier to take the X-rays, regardless of the sequence in which the doctor has requested them. It is common practice for the technician to take the X-rays with as little effort as possible and in a sequence in which the burden on the patient is minimized. Since the recumbent position sensor unit 105 is used for only the "cervical vertebra, foramen," and at this time the patient must be moved a great deal and the position of the X-ray tube must be substantially changed, it is efficient for X-ray photography other than the "cervical vertebra, foramen" to be performed continuously to reduce the burden on the patient. For example, X-ray photography is performed in the sequence "cervical vertebra, fronts"→"cervical vertebra, right rear oblique region"→"cervical vertebra, side"→"cervical vertebra, foramen." In this case, after X-ray photography of the "cervical vertebra, four directions" is terminated, the photographs are transferred via the network 110 in the sequence in which they were taken by the imager 111. Consequently, they must be transferred to film and must be rearranged in the sequence in which the doctor wishes to examine them to perform diagnosis.

In recent years, there have been cases in which networks are constructed with intra-hospital information systems called "HIS" and radiology information systems called "RIS," and requested data from the diagnosis department and patient information from the HIS server are transmitted via the network and are input. Even in this case, the above-described problems remain.

In a manner as described above in the first X-ray photography situation, there is a problem in that proper positioning cannot be performed efficiently when the predetermined photographic sequence is inconvenient for the technician; therefore, the photographing efficiency is decreased, and the burden on the patient is substantial. In the second X-ray photography situation, effort is subsequently required to rearrange the sequence of the image films into that which the doctor wishes to see, and this is also inconvenient. Another problem is that there is no effective means to confirm the order of the part currently being X-rayed and to confirm which part is photographed last. In addition, a problem arises in that when an X-ray must be retaken, this retake must be performed before the next part is X-rayed.

As described above, there are problems in that when X-ray photography is to be performed in a requested sequence, the photographing efficiency may be decreased, and in that the rearrangement of the sequence to that in which the doctor will view the images after the X-ray photographs are taken is very complicated. In addition, problems occur in that it cannot be confirmed which part in the photographing order is currently being photographed, and in that when the image is blurred, retake cannot be performed quickly. Such problems occur not only in the above-described examination apparatus, but also in other photography, for example, in a case in which images from a consumer digital camera are printed out.

SUMMARY OF THE INVENTION

An object of the present invention is to overcome the above-described problems.

Another object of the present invention is to provide an apparatus capable of taking X-ray photographs using a plurality of photographic methods with easy operation, which are easy to understand for both the requestor (for example, a doctor) and the operator (for example, a technician).

Another object of the present invention is to provide an apparatus capable of taking a large number of X-ray photographs, in which it is easy to determine the photographs which are yet to be taken in the photographing order, the portion currently being photographed, and the portions which have already been photographed.

Another object of the present invention is to provide an image processing method and apparatus having new features, a medium, and an X-ray photographic system.

To achieve the above-mentioned objects, according to a first aspect of the present invention, there is provided an examination system comprising: an input device for inputting the sequence of a plurality of examination methods for a patient; a changing device for changing the input sequence; a performing device for performing the examination in accordance with the changed sequence; and an output device for outputting in a desired sequence a plurality of examination results performed by the performing device.

According to a second aspect of the present invention, there is provided an image processing apparatus comprising: an instruction device for instructing a plurality of photographs be taken with respect to an object image in a predetermined sequence; a changing device for changing the sequence by the instruction device; and an output device for outputting in the predetermined sequence a plurality of images photographed in accordance with a sequence changed by the changing device.

According to a third aspect of the present invention, there is provided an image processing method, comprising the steps of: instructing a plurality of photographs be taken with respect to an object image in a predetermined sequence; receiving a changing of sequence by the instruction device and changing the sequence; and outputting in the predetermined sequence a plurality of images photographed in accordance with a sequence changed by the changing device.

According to a fourth aspect of the present invention, there is provided a computer-executable storage medium for storing a program, the program comprising the steps of: instructing a plurality of photographs be taken with respect to an object image in a predetermined sequence; receiving a changing of sequence by the instruction device and changing the sequence; and outputting in the predetermined sequence a plurality of images photographed in accordance with a sequence changed by the changing device.

According to a fifth aspect of the present invention, there is provided a photographic system for irradiating a patient with X-rays and for digitally obtaining an X-ray transmitted image, the photographic system comprising: an X-ray photographic apparatus for performing X-ray photography in given examination units; an apparatus for inputting, to the X-ray photographic apparatus, patient data and photographic request information from which setting parameters required for the X-ray photographic apparatus to perform a photography can be created; an operation device for displaying the system status and for performing an operation; an input device for inputting photographic request information formed of a plurality of photographic requests with respect to one patient data; a creation device for creating setting parameters required to perform photography from the plurality of input photographic requests; and a device for calling and setting the created setting parameters.

With such a construction, it is possible to efficiently take X-ray photographs in a sequence desired by the photographer (technician) regardless of the sequence in the requested photographic order.

The above and further objects, aspects and novel features of the invention will become more apparent from the following detailed description when read in connection with the accompanying drawings.

BRIEF DESCRIPTION OF THE DRAWINGS

FIGS. 2A and 2B show the content of photographic request information.

FIG. 10 shows a photographing order conversion table.

DESCRIPTION OF THE PREFERRED EMBODIMENTS

First Embodiment

Figure 1:
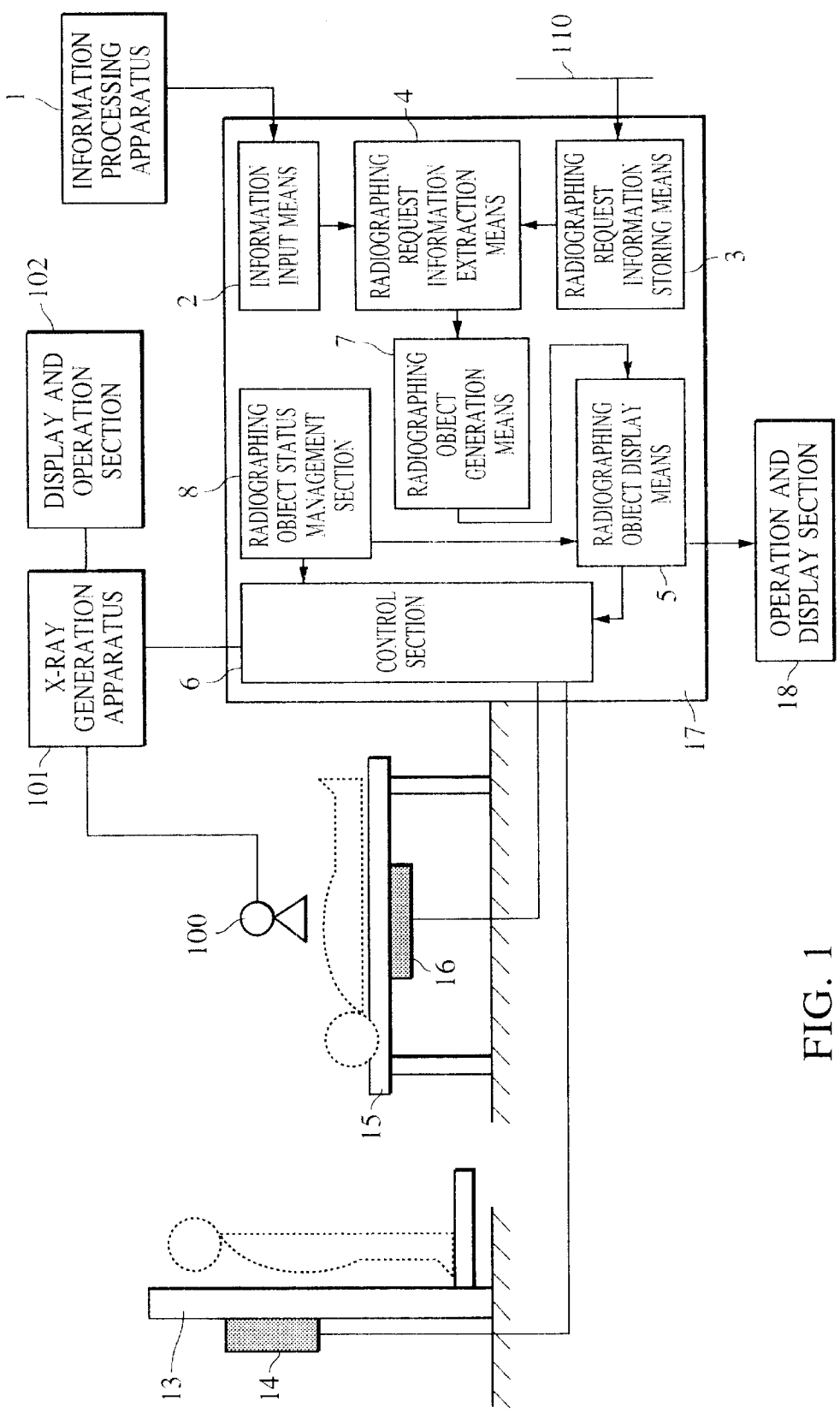
FIG. 1 is a configuration view of an X-ray photographic system according to a first embodiment of the present invention.

FIG. 1 shows the system configuration of an X-ray photographic system according to a first embodiment of the present invention.

Figure 12:
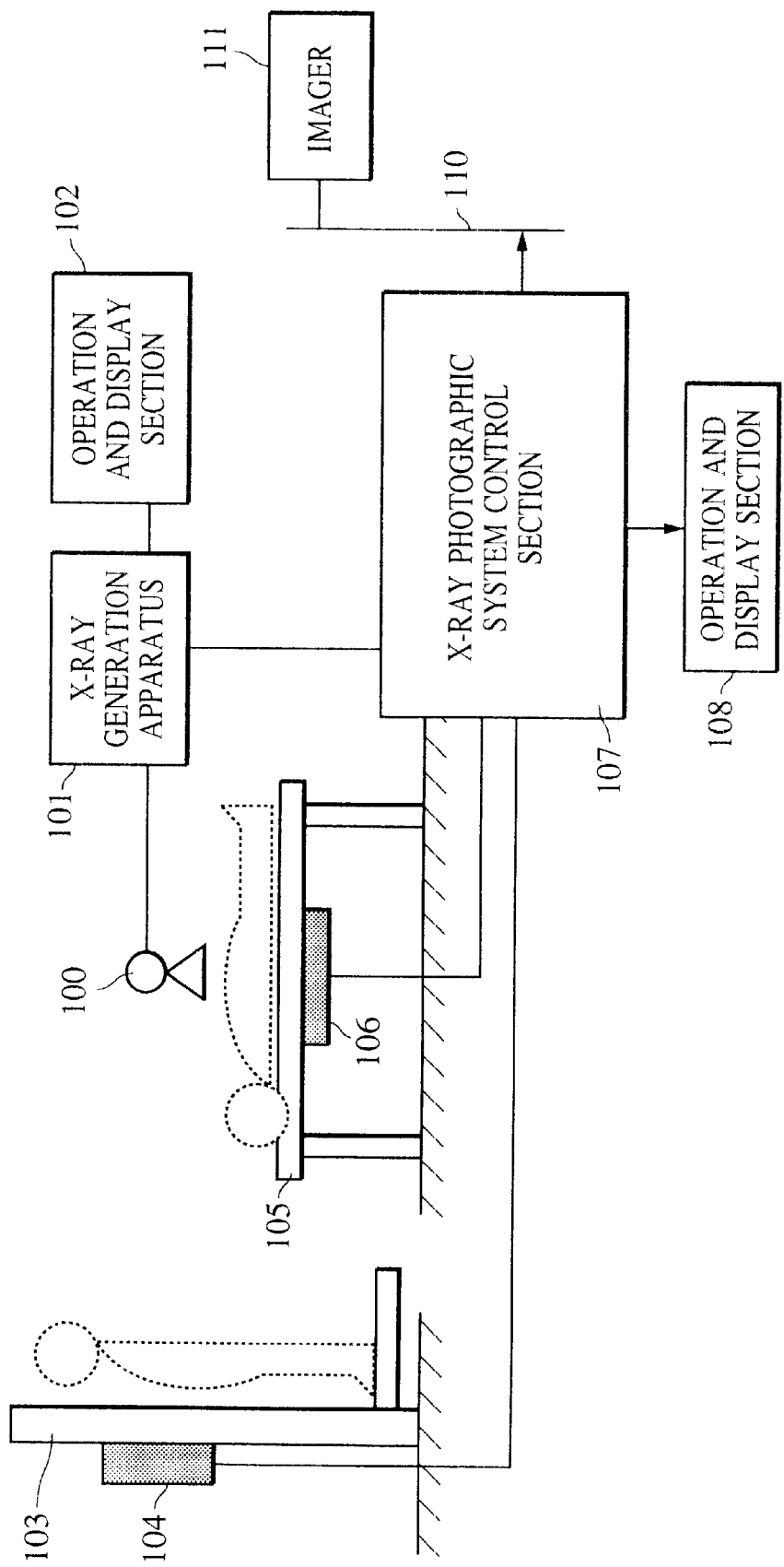
FIG. 12 shows an X-ray photographic system, which is a comparative example of the present invention.

Components in FIG. 1 which are the same as those of FIG. 12 described earlier designate the same. This X-ray photographic system (radiography system) comprises a standing position sensor unit 13, a recumbent position sensor unit 15, an X-ray generation apparatus 101, an operation and display section 102 of the X-ray generation apparatus, a control section 17 of an X-ray photographic (radiography) apparatus, an operation and display 18 of the X-ray photographic apparatus, and an information processing apparatus 1.

In FIG. 1, reference numeral 1 denotes an information processing apparatus for reading the contents of magnetic stripes of a magnetic card, and reference numeral 2 denotes information input means for inputting an examination ID read by the information processing apparatus 1. Reference numeral 3 denotes photographic request information storing means for inputting and memorizing photographic request information input via a network 110. A trigger by which the photographic request information is input may be from the X-ray photographic apparatus control section 17 or may be from a server of the network 110 Reference numeral 4 denotes photographic request information extraction means which functions to extract desired photographic request information from the photographic request information stored in the photographic request information storing means 3 on the basis of the examination ID information input by the information input means 2. The examination ID is an identification number of the photographic request information. The extracted photographic request information is formed of one patient information, and one or more photographic request objects indicating the photographic contents or a photographic request menu. The photographic request menu is formed of a plurality of photographic request objects, for example, items of the photographic request menu include a photographing of cervical vertebra in four directions discussed in the comparative example. The first photographic request object represents a photographing unit. and is often classified by the photographic region name or by the photographic region name and the photographic method. This photographic request object has a unique photographic request name or a photographic request object ID as an identification number for the purpose of identification. The photographic conditions and the image processing parameters may be or may not be entered. When the photographic conditions and the image processing parameters are entered, a search is performed in the previous photography, and the photographic conditions and the image processing parameters at that time are set. If it is a first photography, the standard photographic conditions which are the default values for each photographic request object ID are entered. When the photographic conditions and the image processing parameters are not entered, these items are created based on the photographic request object ID through a photographic object creation means 7 in the X-ray photographic system.

Reference numeral 7 denotes a photographic object creation means for conversion from a photographic request object ID into a photographic object ID. A unique symbol, in addition to the photographic conditions, such as the tube voltage, the tube current, the irradiation time, and image processing conditions, is provided in the obtained photographic object ID, and a photographic object having the symbol displayed thereon is created on the operation and display section 18 of the X-ray photographic apparatus. The symbol may of course be graphics rather than text. Reference numeral 8 denotes a photographic object status management section for managing the status of each of the photographic objects. Reference numeral 5 denotes a photographic object display means for producing a display corresponding to the status from the photographic object status management section 8. Reference numeral 6 denotes a control section for sending and setting the photographic conditions, such as the tube voltage, the tube current, and the irradiation time, or the selected photographic object ID to the X-ray generation apparatus 101 and the sensor panels 13 and 15, and for sending the image processing parameters to the control section 6 in order to specify image processing.

FIGS. 3, 4, 5, 6, and 7 are detailed views of an operation and display section 18 of an X-ray photographic system of FIG. 1. Reference numeral 111 denotes a touch panel formed of a liquid-crystal display and an analog-resistance-film-type touch sensor sheet. Reference numeral 112 denotes a mouse. Reference numeral 113 denotes cables, such as a power supply and a control line. The display is performed by the touch panel 111, and the operation can be performed from either the touch panel 111 or the mouse 112. The cables 113 comprise a power supply, a VGA cable, a serial cable for controlling the touch panel, and a serial cable for a mouse. Reference numeral 114 denotes a photographic image display area for displaying the photographed image. Reference numeral 115 denotes a patient information display area for displaying the patient information. Reference numeral 116 denotes a photographic object parameter display area for displaying the parameter of the photographic object. Reference numeral 117 denotes a photographic object display area for displaying photographic objects of one patient in a list according to the status. Reference numeral 118 denotes a message area for displaying the status of the system and a message. Reference numeral 119 denotes a change switch which is used when the photographic conditions and the image processing parameters are changed.

Figure 9:
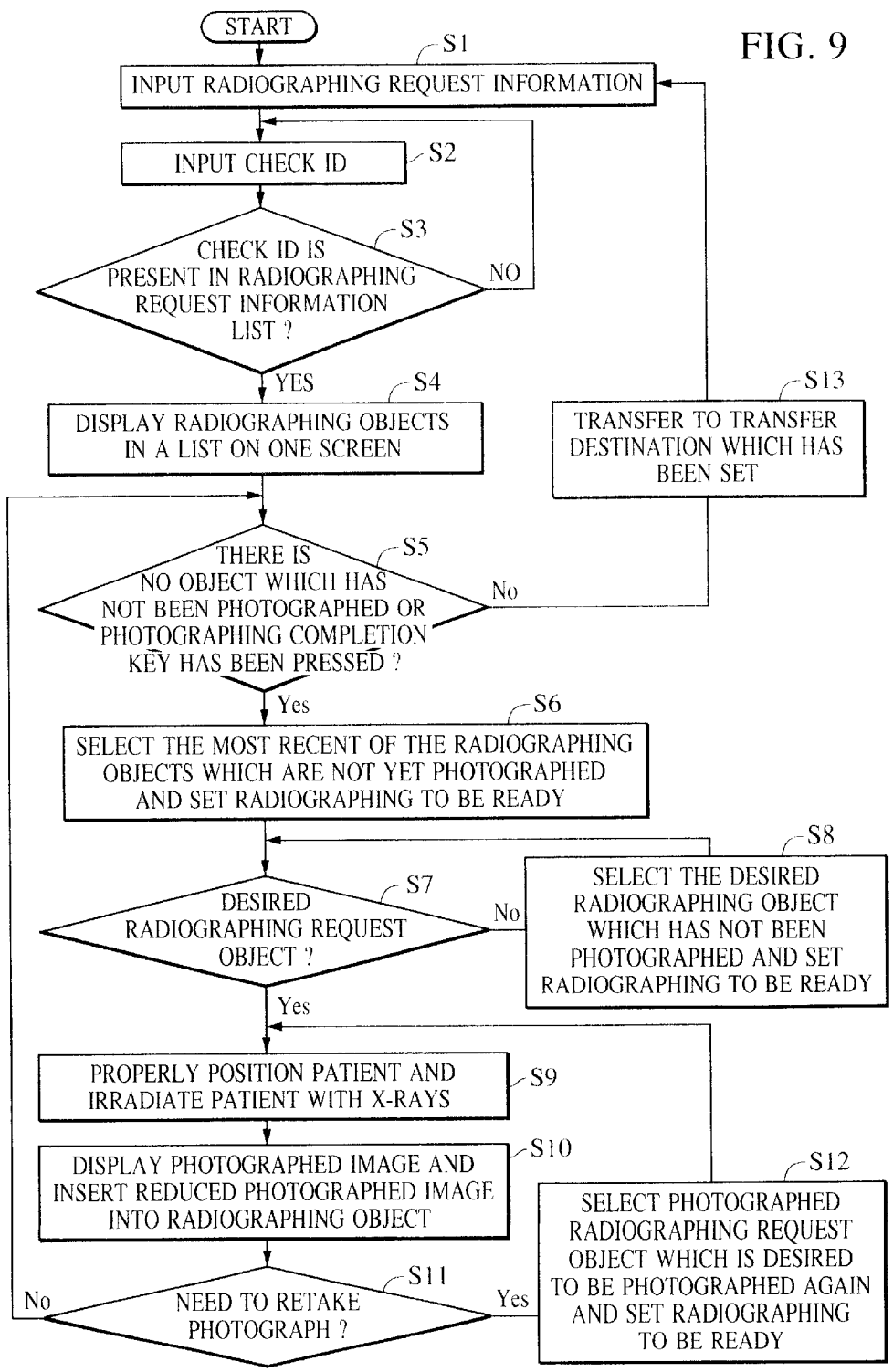
FIG. 9 is a flowchart according to the first embodiment of the present invention.

FIG. 9 is a flowchart according to the first embodiment of the present invention.

Referring to FIGS. 3, 4, 5, 6, and 7 above, the first embodiment of the present invention is described below. A case is described in which cervical vertebrae in four directions are to be photographed, which was described in the comparative example.

An X-ray image is formed by representing differences in the transmittance of the type of the tissue structure in the body of the patient and the thickness thereof as a photographic density. It is important for a good X-ray image that as much information as possible be displayed in a readily visible manner. The position of the patient, the direction of X-ray irradiation, photographic conditions, etc., exert large influences thereon. The photographic posture of the patient differs according to the region for the object of photography, the photographic direction, and the irradiation method, and further, according to the body type of the patient. For example, in the "cervical vertebra, fronts" photography, the patient is made to stand facing the X-ray generation apparatus, the head is slightly raised so that the forehead is horizontal to the sensor panel, the ends of the cutting teeth of the middle upper jaw are adjusted so that the plane including the right and left nipple-shaped projections becomes horizontal, and further, the angle and position of the X-ray tube 100 is adjusted so that X rays can be emitted to the fourth cervical vertebra of the patient from 15° below the fourth cervical vertebra. If the photographic posture is unnatural, the alignment of the body of vertebra cannot be faithfully represented or the region which should be taken note of is hidden, thereby obstructing a diagnosis. The combination of this photographing posture and the irradiation angle is sometimes called a "photographic method".

Examples of the photographic conditions include the setting of the X-ray generation apparatus, such as the tube voltage, the tube current, and the irradiation time; the setting of the irradiation area and the threshold value of the photo-timer; the size of an image to be obtained; and the grid movement speed. In the case of a photographic apparatus capable of digitally obtaining an X-ray image, image processing to be performed on the obtained image exerts a large influence. Examples of image processing include a white correction process, a sensor output correction process such as a gain correction process, a gradation process, changing of type of a density conversion curve, changing of density and contrast, DR compression, and QA processing such as highlight processing. The above-described photographic conditions and the image processing are often determined by the photographic regions, the photographic methods, and the physique of the patient. Accordingly, the photographic request issued from the doctor includes the photographic regions, the photographic methods, and the physique of the patient.

When patient reception has been completed, the patient proceeds to the surgery department and submits a patient's case record and a magnetic card, in which the ID number of the patient is recorded, to the receptionist of the surgery department. The doctor calls the personal data of the patient inside the server of the network of the intra-hospital information system called "HIS" by using the patient ID number of the magnetic card as the search key at the terminal. The doctor performs a medical examination while using this personal data as a reference. When photography of cervical vertebra in four directions is to be performed as a result of the medical examination, the doctor issues the photographic request information from the terminal to the radiation section. For example, it is assumed that the photographic request information is formed of four photographic request objects: the patient name "Taro Kanon" as the patient information, the ID number "123456789", the physique "normal", and the photographing order "cervical vertebra AP," "cervical vertebra, foramen," "cervical vertebra LR," and "cervical vertebra, right rear oblique region." At this time, the examination ID "0000001" is issued. This is a number different from patient to patient, and is recorded on the magnetic card possessed by the patient. The doctor, after issuing the order, passes this magnetic card to the patient and instructs the patient to proceed to the radiation section.

This photographic request information issued from the terminal of the surgery department is transferred to the X-ray photographic system of the photographic room shown in FIG. 1 via the intra-hospital information system HIS and the radiology information system RIS. This photographic request information is stored In the photographic request information storing means 3 of FIG. 1. On the other hand, when the patient arrives at the photographic room, the technician loads the magnetic card into the information processing apparatus 1 in order to read the examination ID number. The read examination ID number is immediately input via the information input means 2. Then, in the photographic request information extraction means 4, the photographic request information of the patient is extracted by finding a matching examination ID number from the stored photographic request Information. The photographic object creation means 7 creates a corresponding photographic object by referring to the photographic request object ID, the photographic request name, the physique of the patient, etc., contained in the extracted photographic request information. At this time, when the photographic conditions and the image processing parameters are not contained in the photographic request object, default values for each photographic object are set. In a case in which photography of any one of the recumbent position and the standing position is possible as in the "cervical vertebra, foramen," the default value for the type of the sensor is also present. The photographic objects are displayed in a photographic method object display section 117 shown in FIGS. 2A and 2B in the sequence in which the doctor has instructed by the photographic object display means 5. At this time, the status management section 8 sets the first photographic object to the "selected state" and sets the status of the photographic objects other than that to the "photographic wait state". For example, the "selected state" is displayed in a state in which the key is pressed, and the "photographic wait states" is displayed in a state in which the key is not pressed. The parameters called by the photographic object ID are the photographic conditions, the image processing parameters, the photographing range, and the set value of the photo-timer. The photographic conditions are: the tube voltage of 72 kV, the tube current of 160 mA, the irradiation time of 56 msec, and the focal length of 120 cm. The image processing parameters are: Img.Process=D1, 3.0;C10;L5 (as the parameters of Img.Process, for example, the first area is at a density 3.0, the contrast γ=10, and a fifth function is used as the density conversion table). The photographic range is a 2688×2688 pixel area, and only the center of the photo-timer is enabled. If these settings are performed individually, a lot of time and labor is taken, and therefore, all are performed by pressing the photographic object. The parameters are transferred to the X-ray generation apparatus 101 shown in FIG. 1 so that the tube voltage, the tube current, and the irradiation time are set, and the photographic range and the set values of the photo-timer, etc., are sent to the standing position sensor unit 13 used for photography. Also, the image processing parameters are set at this point in time.

Figure 3:
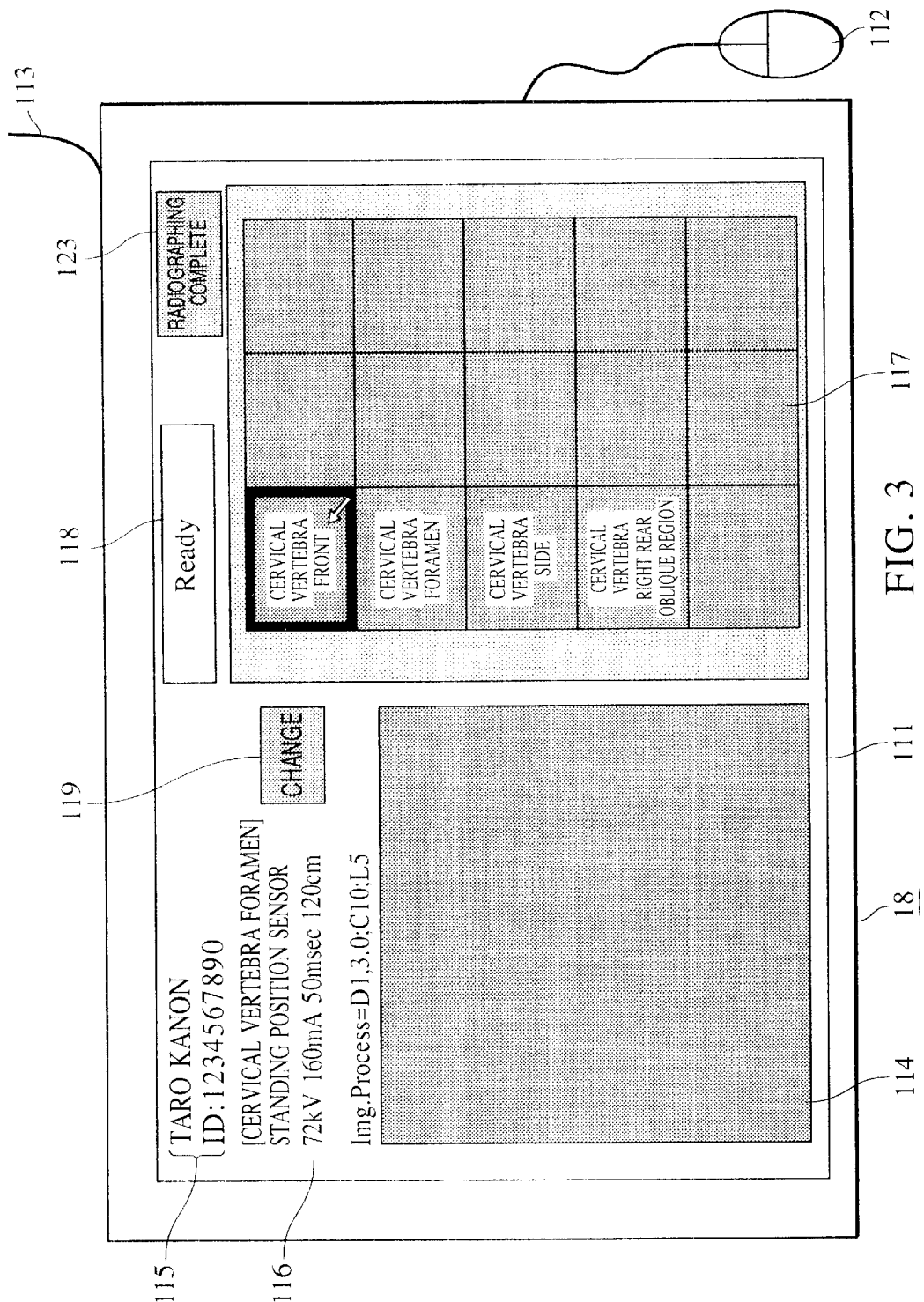
FIG. 3 shows the displayed contents of an operation and display section of the X-ray photographic system at the time a first photograph is taken, according to the first embodiment of the present invention.
Figure 4:
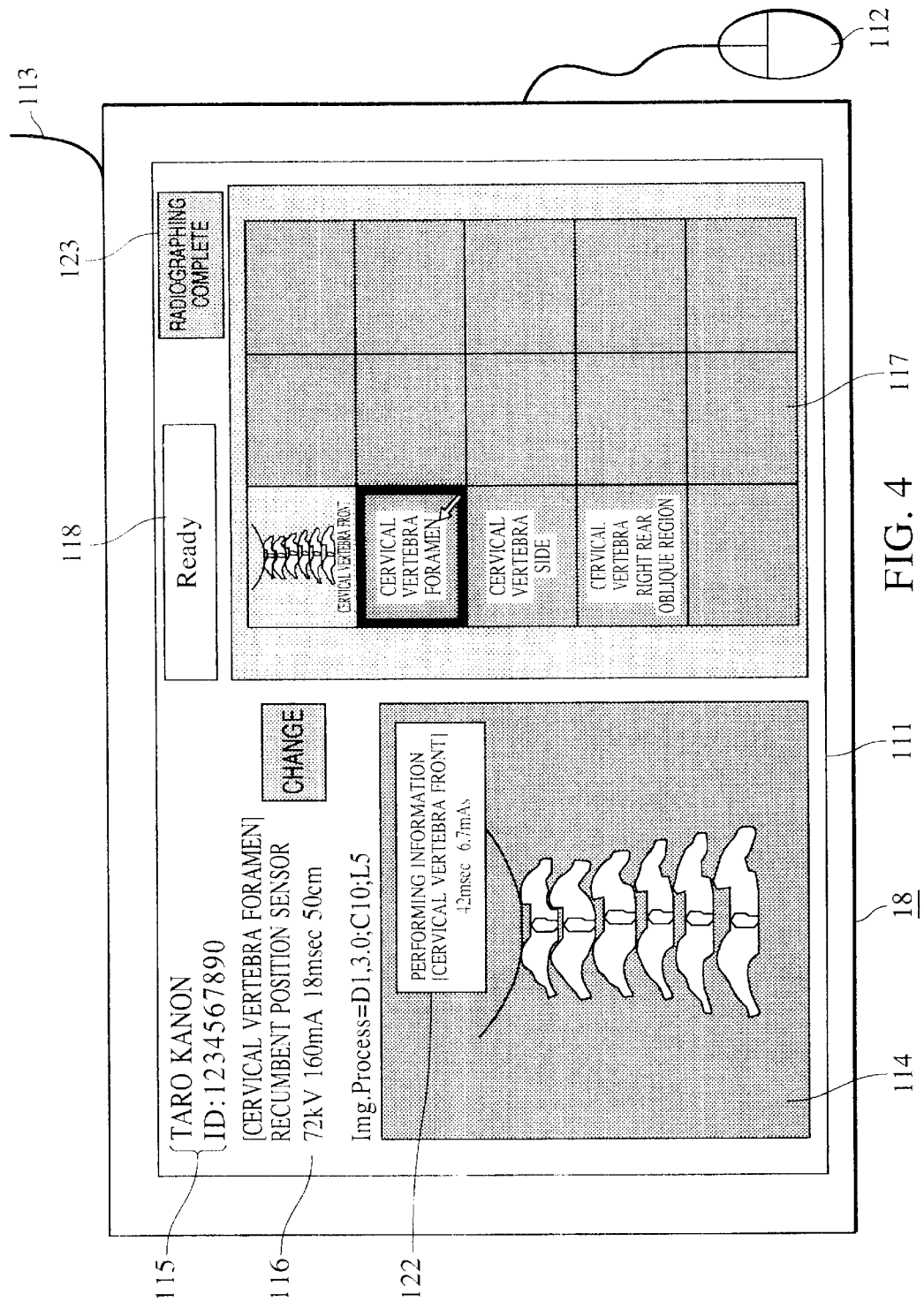
FIG. 4 shows the displayed contents of the operation and display section of the X-ray photographic system after the first photograph has been taken, according to the first embodiment of the present invention.
Figure 5:
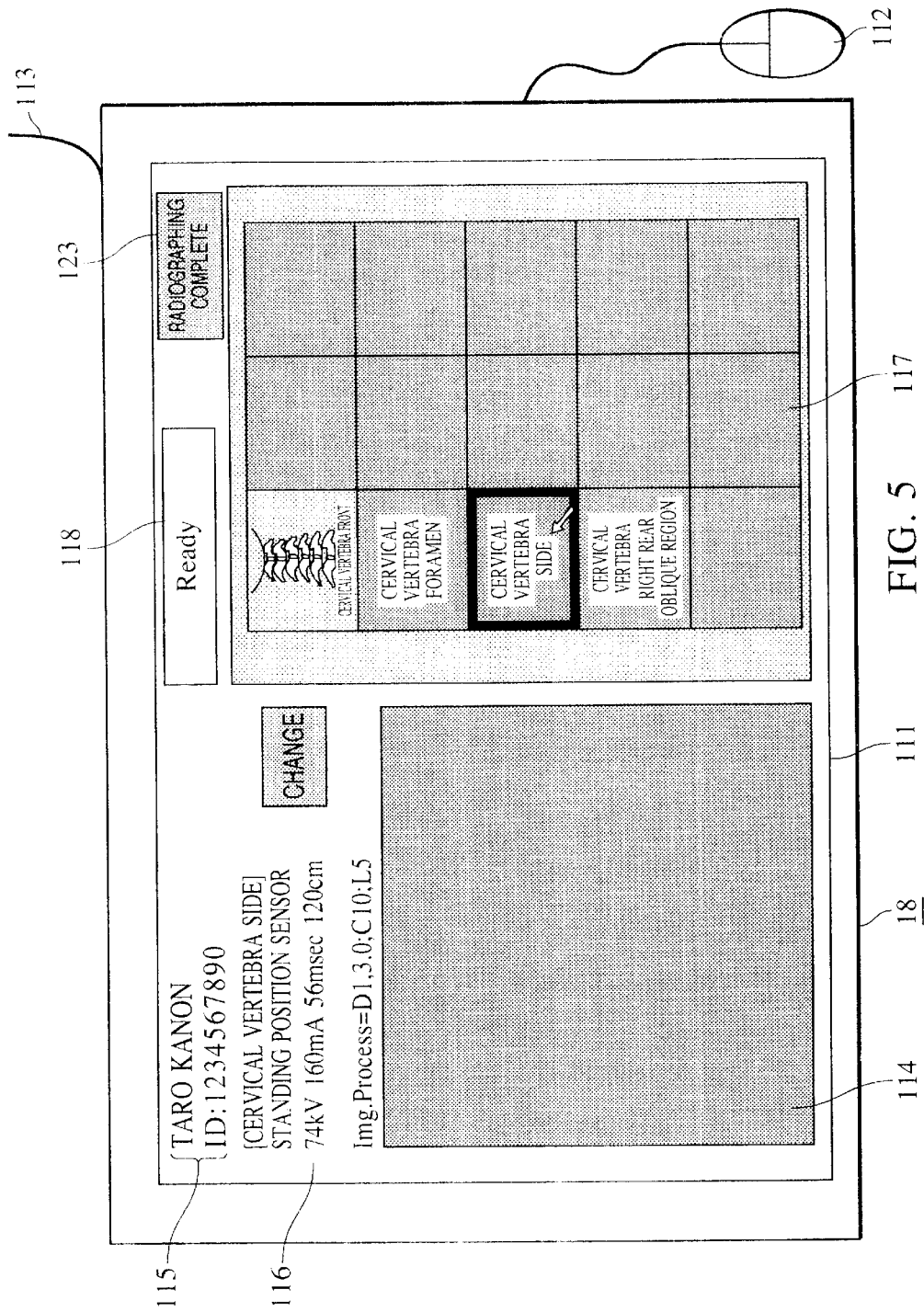
FIG. 5 shows the displayed contents when a second photographic method in the operation and display section of the X-ray photographic system is changed according to the first embodiment of the present invention.
Figure 6:
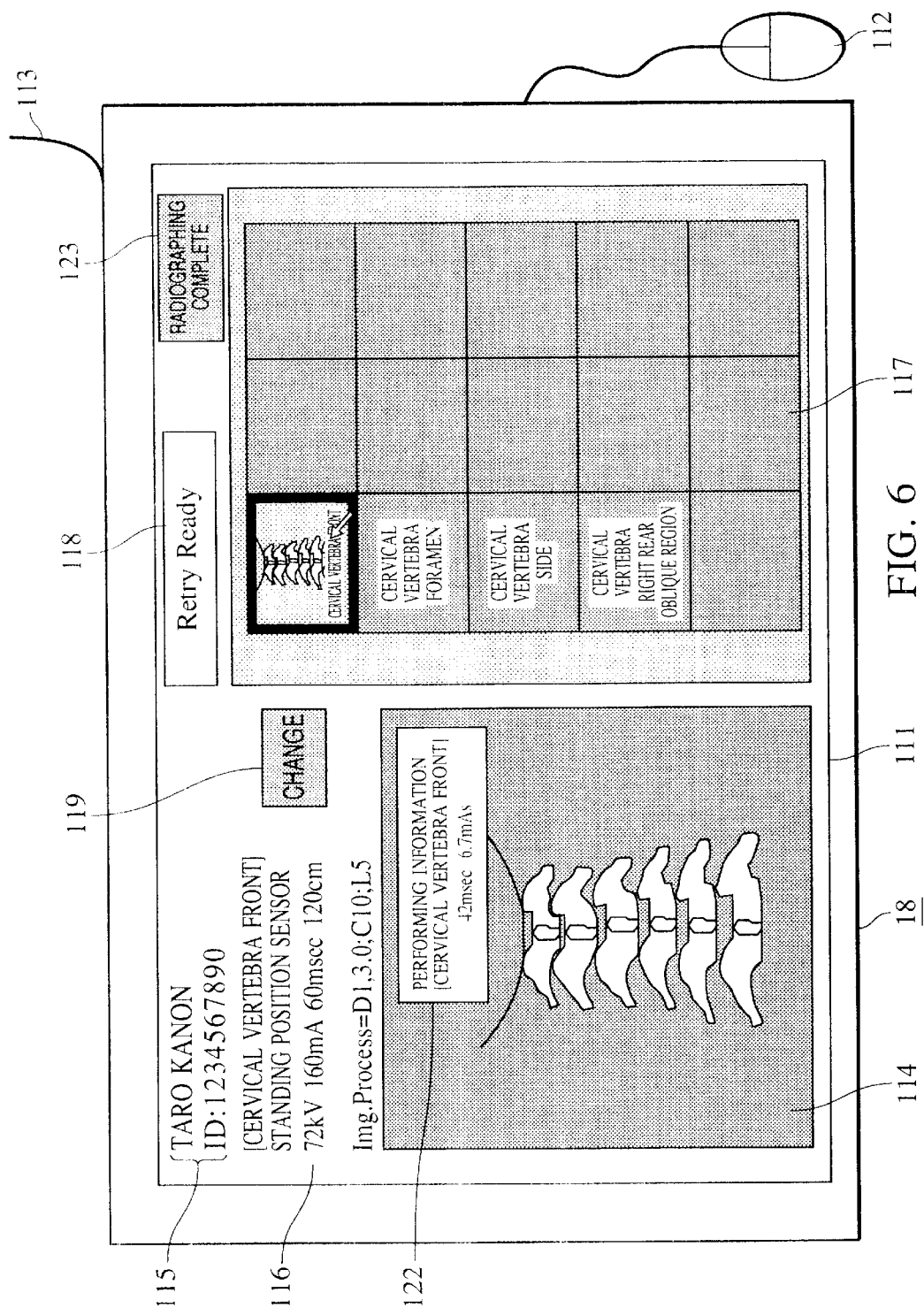
FIG. 6 shows the displayed contents when the first image in the operation and display section of the X-ray photographic system is to be retaken according to the first embodiment of the present invention.
Figure 7:
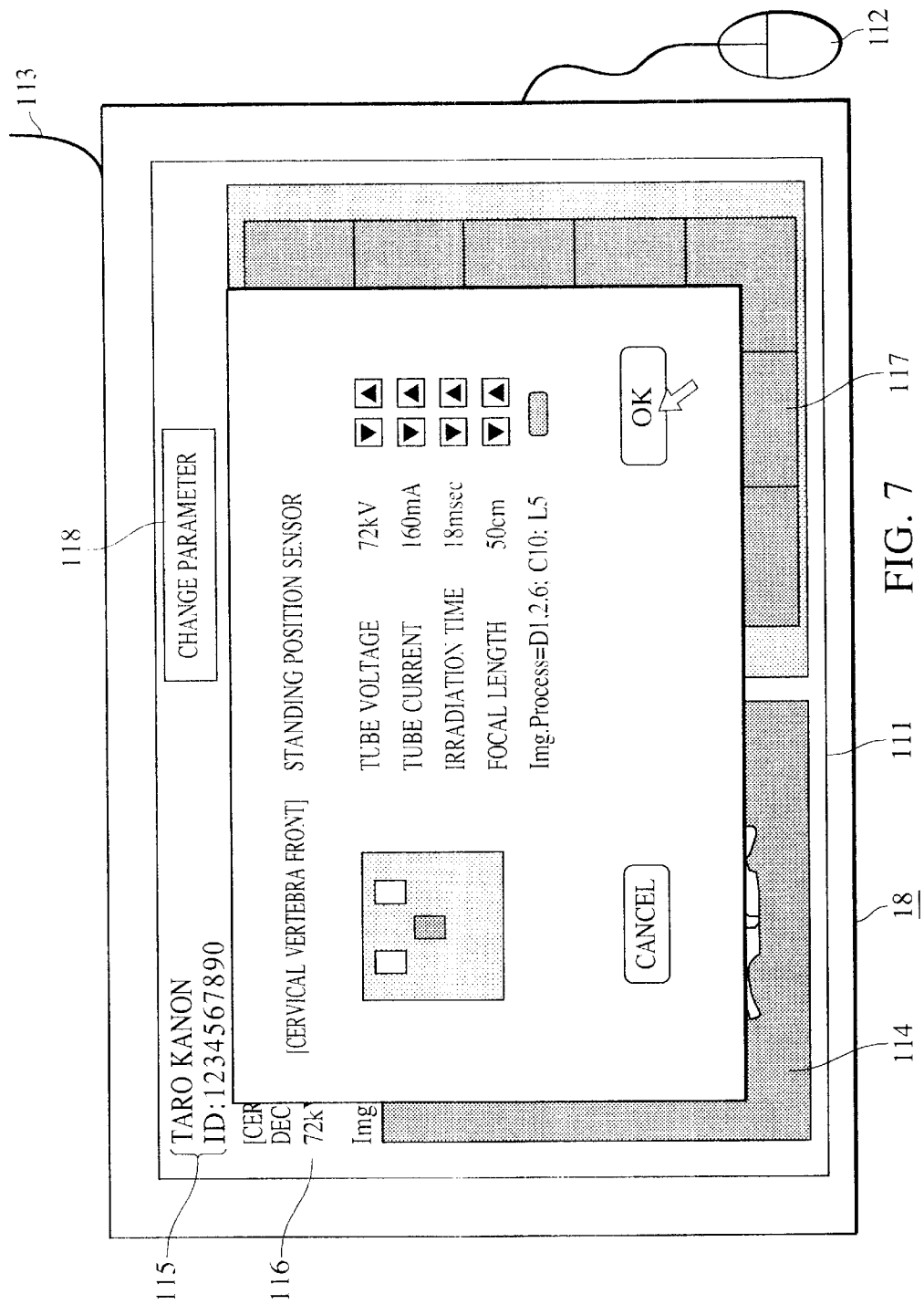
FIG. 7 shows the displayed contents of a change dialogue for a photographic method parameter of the operation and display section of the X-ray photographic system according to the first embodiment of the present invention.

The display at this time is as shown in FIG. 3. The name and the ID number of the patient are displayed in the patient information display area 115; the photographic conditions and the image processing conditions are displayed in the photographic object parameter display area 116; and a state in which the "cervical vertebra, front" is selected is displayed in the photographic object display section 117. If these conditions are OK, the patient is properly positioned, and photography is performed by irradiating X-rays. When, however, a change is required, the change switch 119 is pressed to call a parameter change dialogue such as that shown in FIG. 7 in order to change various parameters. When all are completed, X-rays are irradiated to obtain an X-ray image. The photographed image as shown in FIG. 4 is displayed in the photographic image display area 114, and the photographic object status management section 8 changes the status of the "cervical vertebra, front" of the photographic object to "photographed". Also, since the photographic method object or the "cervical vertebra, front" is changed to "photographed," the photographic object display means 5 displays a reduced image of the "thoracic vertebra, front," instead of displaying the "cervical vertebra, front," and displays performing information, such as the irradiation time and the mAs value, on a performing information window 122 (see FIG. 5) This performing information is also added to the photographic object. Then, the next "cervical vertebra, foramen" is set to the "selected state" on the basis of the information the doctor has requested so that a photographic ready state is reached. Here, if the "cervical vertebra, side" is desired to be photographed earlier, the "cervical vertebra, side" switch of the photographic object display section 117 is pressed. As shown in FIG. 5, the parameters of the photographic object of the "cervical vertebra, side" are then transferred to the X-ray generation apparatus 101 of FIG. 1 as described earlier, so that the tube voltage, the tube current, and the irradiation time are set, the photographing range and the set values of the photo-timer, etc. are sent to the standing position sensor unit 103 used for photography. The image processing parameters are also set at this point in time, and the system changes to a photographic ready state. Furthermore, when a photograph is to be retaken, the "cervical vertebra, front" key in which the reduced image of FIG. 3 is displayed is pressed. Then, since the status of the photographic object of the "cervical vertebra, front" is determined to be "photographed" by the photographic object status management section 8 of FIG. 1. the photographed image of the "cervical vertebra, front" is displayed in the photographic image display area 114, the parameters of the photographic object are displayed in the photographic object parameter display area 116, and the system is made to transition to the re-photographic ready state in the "cervical vertebra, front." FIG. 6 shows the display state at that time. When all the photography has been completed in the above procedure, a photographic completion key 123 is pressed so that the process proceeds to a photographic completion process. The photographed images are rearranged in the requested sequence ("cervical vertebra, front"→"cervical vertebra, foramen"→"cervical vertebra, side"→"cervical vertebra, right rear oblique region") and are output to the image server of RIS and the imager. The patient information, the information of the changed photographic object, etc., together with the image information, are also transferred to the image server. The transfer destination is set in advance on a system setting screen (not shown).

The above sequence is described with reference to the flowchart of FIG. 9. In steps S1 and S2, photographic request information is input from the intra-hospital information system HIS, the radiology information system RIS, etc., and an examination ID is input from input means. When it is determined in stop S3 that there is photographic request information corresponding to the examination ID input in step S2, the photographic objects are displayed in a list in the requested order (step S4). If the photographing key has not been pressed or if there is an object which is not yet photographed, the first photographic object of the objects which are not yet photographed is made selectable (step S6). After a confirmation is made as to whether it is a desired photographic object (step S7), the patient is properly positioned, and a photograph is taken by irradiating X-rays (step S9). After the photograph is taken, the photographed image is displayed, and the reduced image thereof is embedded in the photographic object and is displayed (step S10). When there is no need to re-take (step S11), the process proceeds to the next photographic step (step S5 and subsequent steps). When a re-take is to be performed, the photographed photographic object in which re-taking is desired is selected, and the photographic ready state is set to take a photograph (steps S12, S9, and S10). When there is no photographic object which has not been photographed or when the photographic completion key is pressed (step S5), the photographs are transferred to the transfer destination in the requested sequence (step S13), and photography of the next examination ID is performed.

In a manner as described above, when a plurality of photographs are requested, the display of the photographic object is replaced with the photographed image after the photograph is taken. Consequently, there are advantages in that it can be quickly determined for which of the photographing plans the current photographic method is positioned, re-photographing can be performed at a timing desired by the technician, and it is difficult to make a mistake because the image to be re-taken is displayed. In addition, there is the advantage in that since photographs are transferred to the image server and the imager in the sequence requested by the doctor even if the photographs are taken in any sequence, it is easy for the doctor to diagnose. Here, although a magnetic card is used to find the examination ID, similar advantage can be obtained even if other information recording media, such as bar codes or IC cards, are used.

In the X-ray photographic system described in the first embodiment, a magnetic card is used to find the examination ID, and the photographs are displayed in the photographic method object display section 117 by the photographic object display means 5 in the sequence instructed by the doctor. However, facilities exist in which no magnetic card is used. The reason for this is that there is a risk in that a magnetic card might be lost or magnetic stripes might be damaged. In that case, the oldest photographic request information in the examination order list is selected, the first photographic object of the photographic request is selected, and the system is made to transition to a photographic ready state. If the examination ID is to be changed, the examination list is displayed, and a desired examination ID is selected from the list.

Second Embodiment

The sequence of the photographic request objects is fixed by a doctor and a technician and by implementation after being put into practical use in particular medical facilities. Therefore, it is effective that a correspondence table is created in advance and the photographic order is converted in accordance with the table. This table is referred to when photographic request information is extracted by the photographic request information extraction means 4 in FIG. 1 and when photographs are transferred to the image server and the imager after the photographs are taken. Then, the sequence of the photographic request objects is automatically converted on the basis of the request information and the status of a technician switch 120 and a transfer destination switch 121.

Figure 8:
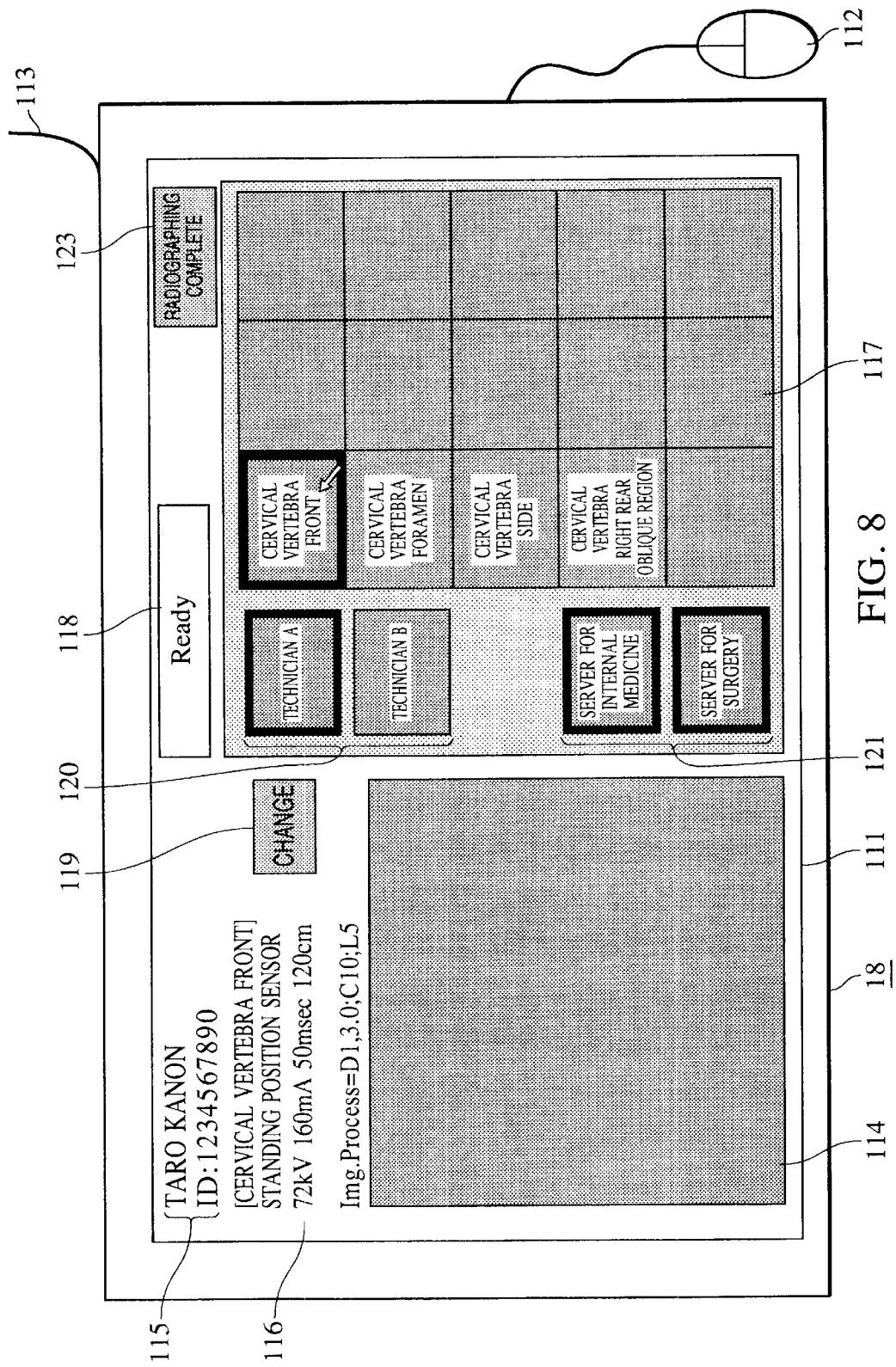
FIG. 8 shows the displayed contents of an operation and display section of an X-ray photographic system according to a second embodiment of the present invention.

FIG. 10 shows an example of this conversion table. In this case, the operation and display section 18 is as shown in FIG. 8. Reference numeral 120 denotes a technician switch, which is a key for identifying a technician who controls the X-ray photographic system. Reference numeral 121 denotes a transfer destination switch, which is a switch for selecting a transfer destination. The default of the transfer destination switch is determined by the photographic request information. Assuming that a technician A is selected as the technician switch 120, when photographic request information of a surgeon A for thoracic vertebra in four directions is received, a display is produced in the sequence of "cervical vertebra, front"→"cervical vertebra, side"→"cervical vertebra, right rear oblique region"→"cervical vertebra, foramen" as in the photographic method object display section 117 of FIG. 8. Also, after the photographs are taken, they are transferred to the requestor in the requested sequence and are transferred to the server shared for surgery in the sequence such as "cervical vertebra, front"→"cervical vertebra, side"→"cervical vertebra, foramen"→"cervical vertebra, right rear oblique region".

Figure 11:
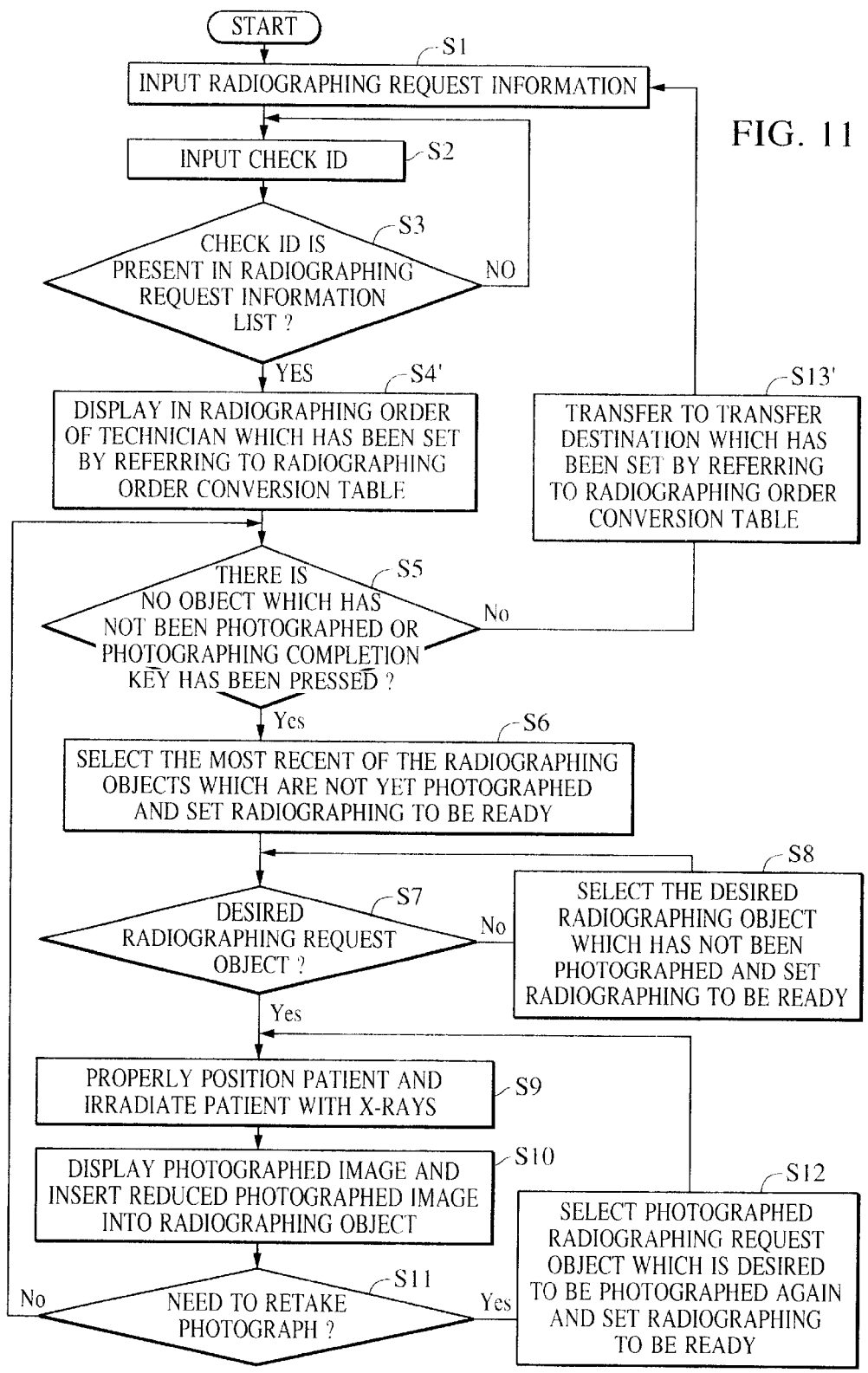
FIG. 11 is a flowchart according to the second embodiment of the present invention.

FIG. 11 is a flowchart according to a second embodiment of the present invention. Steps S4' and S13' are different from those of the first embodiment. By referring to the photographic order conversion table in both steps, the photographic sequence is rearranged in a predetermined sequence desired by the doctor, and transferring is performed in a predetermined sequence.

In a manner as described above, the sequence can be automatically changed and transferred for each transfer destination, thereby yielding the advantage that the operation is easy.

In the above-described embodiments, a system comprising an X-ray photographic apparatus is disclosed. In addition, without being limited to such a system, the present invention can be applied to, for example, a system comprising a consumer digital camera and printer.

An apparatus which changes a prespecified photographic sequence in order to take a photograph and which prints out in a specified sequence different from the sequence in which photography is performed actually is included in the present invention.

Another Embodiment of the Present Invention

The present invention may be applied to a system comprising a plurality of apparatuses (for example, a host computer, an interface apparatus, a reader, a printer, etc.) or to a single apparatus (for example, a copying machine, a facsimile apparatus, etc.).

Also, an embodiment is included within the scope of the present invention, in which program codes of software for realizing the above-described embodiments are supplied to a computer within an apparatus or a system connected to various devices so that the various devices are operated to realize the functions of the above-described embodiments, and the computer (CPU or MPU) of the system or the apparatus causes the various devices to operate in accordance with the stored program.

In this case, the program codes of the software themselves realize the functions of the above-described embodiments, and the program codes themselves and a means, for example, a storage medium storing such program codes, for supplying the program codes to a computer, comprises the present invention.

As storage media for storing such program codes, for example, floppy disks, hard disks, optical disks, magneto-optical disks, CD-ROMs, magnetic tape, non-volatile memory cards, ROMs, etc., may be used.

Not only in a case in which the functions of the above-described embodiments are realized by executing supplied program codes by a computer, but also in a case in which the functions of the above-described embodiments are realized by the program codes in collaboration with an OS (operating system) running in a computer or in collaboration with other application software, it is a matter of course that such program codes are included in an embodiment of the present invention.

In addition, it is a matter of course that a case is also included in the present invention, in which after supplied program codes are stored in a memory provided in a function expansion unit connected to a function expansion board of a computer or connected to a computer or a CPU which is provided in a function expansion board or in a function storage unit, performs a part or the entirety of actual processing in accordance with the instructions of the program codes, and the functions of the above-described embodiments are realized by the processing.

According to the present invention, examination can be performed actually in a sequence which is different from a prespecified examination sequence, and the output of images can also be performed in a desired sequence. Consequently, ease of operation of examination can be improved.

Furthermore, according to the present invention, even if the photographic sequence is changed from the prespecified sequence, photographed images can be output in such a prespecified sequence. Consequently, arranging and managing photographed images is easy.

In addition, according to the present invention, since the photographic sequence can be changed at a user's discretion regardless of the photographic sequence of the issued photographic request, the photographic efficiency is improved, and the burden on proper positioning of a patient can be reduced. Further, photographs can be output in a desired sequence at a desired place without performing complex operations, yielding the advantage that the diagnosis efficiency is increased.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included within the spirit and scope of the invention as hereafter claimed. The scope of the following claims is to be accorded the broadest interpretation so as to encompass all such modifications, equivalent structures and functions.

What is claimed is:

1. An examination apparatus, comprising:

input means for inputting examination request information including a plurality of examination methods for a patient;

selection means for selecting one from the plurality of examination methods, wherein said selection means is capable of selecting one from the plurality of examination methods in an arbitrary order;

performing means for performing the selected examination method and obtaining a result therefrom; and output means for outputting the results of the plurality of examination methods in a predetermined order regardless of an order in which the performing means has performed the plurality of examination methods.

2. An examination apparatus, comprising:

input means for inputting examination request information including a plurality of examination methods arranged in an order for a patient;

handling means for handling each of the plurality of examination methods as an examination method object and for attaching a status to each of the examination method objects;

display means for displaying the examination method objects of the plurality of examination methods;

changing means for changing a display format of each of the examination method objects according to the status;

selection means for selecting one of the examination method objects;

performing means for performing examination in accordance with an examination condition determined by the selected examination method object and in accordance with an examination mode determined by the status of the selected examination method object; and output means for outputting a plurality of examined examination method objects in the order in the examination request information regardless of an order in which the performing means has performed the plurality of examination methods.

3. An examination apparatus according to claim 2, wherein types of the status attached to each of the examination method objects include at least an examination wait state and an examination termination state, and the display format of each of the examination method objects and/or the examination mode is changed by the attached status.

4. An examination apparatus according to claim 3, wherein said display means divides a particular area on a display screen of an operations console into a plurality of areas and causes the respective areas to be linked with the plurality of examination method objects, and wherein when the status is in the examination wait state, a symbol indicating an examination method is displayed, and when the status is in the examination termination state, an examination result such as an examination image is displayed instead of the symbol.

5. An examination apparatus according to claim 4, wherein a mouse and/or a touch screen are provided, each of the respective areas on the display screen of the operations console is made user-selectable, and when the symbol indicating an examination method is selected, examination is set ready, and when the examination result is selected, reexamination is set ready.

6. An examination apparatus according to claim 2, wherein said examination apparatus is a radiographic apparatus comprising a radiation generation unit and a radiographic unit.

7. An examination apparatus, comprising:

input means for inputting examination request information including a plurality of examination methods arranged in an order for a patient;

handling means for handling each of the plurality of examination methods as an examination method object and for attaching a status to each of the examination method objects;

display means for displaying the examination method objects of the plurality of examination methods;

format changing means for changing a display format of each of the examination method objects according to the status;

order changing means for changing the order into a changed order;

performing means for performing examination in accordance with an examination condition determined by the examination method object selected on the basis of the changed order and in accordance with an examination mode determined by the status of the selected examination method object; and output means for outputting a plurality of examined examination method objects in the order in the examination request information regardless of the changed order.

8. An examination apparatus according to claim 7, wherein types of the status attached to each of the examination method objects include at least an examination wait state and an examination termination state, and the display format of each of the examination method objects and/or the examination mode is changed by the attached status.

9. An examination apparatus according to claim 8, wherein said display means divides a particular area on a display screen of an operations console into a plurality of areas and causes the respective areas to be linked with the plurality of examination method objects, and wherein when the status is in the examination wait state, a symbol indicating an examination method is displayed, and when the status is in the examination termination state, an examination result such as an examination image is displayed instead of the symbol.

10. An examination apparatus according to claim 9, wherein a mouse and/or a touch screen are provided, each of the respective areas on the display screen of the operations console is made user-selectable, and when the symbol indicating an examination method is selected, examination is set ready, and when the examination result is selected, reexamination is set ready.

11. An examination apparatus according to claim 7, wherein said examination apparatus is a radiographic apparatus comprising a radiation generation unit and a radiographic unit.

12. An image processing apparatus comprising:

input means for inputting request information including a plurality of requests each of which corresponds to an image to be processed arranged in an order;

changing means for changing the order as input by said input means into a changed order;

processing means for processing an image in accordance with the changed order and obtaining a processed image; and output means for outputting a plurality of images processed by said processing means in the order as input by said input means regardless of the changed order.

13. An image processing apparatus according to claim 12, wherein said output means comprises recording means for recording the plurality of processed images in a medium.

14. An image processing apparatus according to claim 12, wherein said changing means changes the order in accordance with a manual instruction from a user.

15. An image processing apparatus according to claim 12, wherein said processing means comprises means for performing photography.

16. An image processing apparatus according to claim 15, wherein said photography is radiography.

17. An image processing method, comprising the steps of:
inputting request information including a plurality of requests each of which corresponds to an image to be processed arranged in an order;
changing the order as input into a changed order;
processing an image in accordance with the changed order and obtaining a processed image; and
outputting a plurality of images processed in said processing step, in the order as input in said input step regardless of the changed order.

18. A computer-readable storage medium storing a program for executing an image processing method, said method comprising the steps of:
inputting request information including a plurality of requests each of which corresponds to an image to be processed arranged in an order;
changing the order as input into a changed order;
processing an image in accordance with the changed order and obtaining a processed image; and
outputting a plurality of images processed in said processing step, in the order as input in said input step regardless of the changed order.

19. A radiographic apparatus for obtaining a radiograph of an object, comprising:
input means for inputting radiographic request information including a plurality of radiographic requests arranged in an order for a patient;
performing means for performing radiography in accordance with the input radiographic request information and obtaining a radiograph, wherein said performing means is capable of performing radiography for the plurality of radiographic requests in an arbitrary order; and
output means for outputting radiographs of the plurality of radiographic requests obtained by the performing means, in a predetermined order regardless of an order in which the performing means has performed radiography for the plurality of radiographic requests.

20. A radiographic apparatus according to claim 19, further comprising:
creation means for setting parameters required to perform radiography from the input radiographic request information; and
calling means for calling the set parameters, wherein said calling means includes a setting object showing a symbol by which a type of the radiographic request is designated.

21. A radiographic apparatus according to claim 19, further comprising setting means for setting an order of the radiographic requests in which the performing means should perform radiography in accordance with the input radiographic request information.

22. A radiographic apparatus according to claim 19, further comprising display means for displaying a plurality of objects showing symbols by which types of the radiographic requests are designated for a patient.

23. A radiographic apparatus according to claim 22, wherein said display means divides a particular area on a display screen of an operations console into a plurality of areas and displays in the respective areas the objects corresponding to the radiographic requests.

24. A radiographic apparatus according to claim 19, further comprising display means for displaying a setting object showing a symbol by which a type of the radiographic request is designated in a preset order regardless of the order as input by the input means.

25. A radiographic apparatus according to claim 19, further comprising:
   display means for displaying a setting object showing a symbol by which a type of the radiographic request is designated; and
   changing means for changing a display format of the setting object in accordance with a status of the setting object.

26. A radiographic apparatus according to claim 25, wherein said display means divides a particular area on a display screen of an operations console into a plurality of areas and causes the respective areas to be linked with a plurality of setting objects, and said changing means causes the setting object to display a symbol indicating the radiographic request when the status of the setting object is in a radiographing wait state, and causes the setting object to display a radiographic result such as a radiograph instead of the symbol when the status of the setting object is in a radiographing termination state.

27. A radiographic apparatus according to claim 25, wherein types of the status include at least a radiographing wait state and a radiographing termination state, and the display format of the setting object and/or a radiographing mode is changed in accordance with the status.

28. A radiographic apparatus according to claim 19, further comprising order changing means for changing an order of the radiographic requests into a changed order in which said performing means is to perform radiography in accordance with the input radiographic request information.

29. A radiographic apparatus according to claim 19, wherein the predetermined order of the output means is determined in accordance with at least one of a request source and a transfer destination of radiographs.

30. A radiographic apparatus according to claim 19, wherein the predetermined order of the output means is the order as input by said input means.

31. A radiographic apparatus according to claim 19, further comprising retaking means for retaking a radiograph for a taken radiograph.

32. A radiographic apparatus according to claim 26, further comprising pointing means used by a user for selecting one of the plurality of setting objects, wherein when the setting object displaying the symbol is selected, radiographing is set ready, and when the setting object displaying the radiographic result is selected, reradiographing is set ready.

33. A radiographic apparatus according to claim 19, wherein the radiographic apparatus is connected to a hospital information system, such as an intra-hospital information system or radiology information system.

34. An examination apparatus, comprising:
   input means for inputting examination request information including a plurality of examination methods arranged in an order for a patient;
   changing means for changing the order into a changed order;
   performing means for performing examination in accordance with the changed order and obtaining results therefrom; and
   output means for outputting results of the plurality of examination methods obtained by the performing means, in a predetermined order regardless of the changed order.

35. An examination apparatus according to claim 1, wherein the predetermined order is the same as the order in the examination request information.

36. A computer-readable storage medium storing a program for executing an image processing method, the method comprising the steps of:
   inputting request information including a plurality of requests each of which corresponds to an image to be processed;
   selecting one from the plurality of requests, wherein an order in which one from the plurality of requests is selected is changeable;
   processing an image in accordance with the selected request and obtaining a processed image; and
   outputting a plurality of processed images in a predetermined order regardless of an order in which the plurality of images corresponding to the plurality of requests have been processed.

37. An image processing apparatus, comprising:
   input means for inputting request information including a plurality of requests each of which corresponds to an image to be processed;
   selection means for selecting one from the plurality of requests as input by said input means, wherein said selection means is capable of selecting one from the plurality of requests in an arbitrary order;
   processing means for processing an image in accordance with the selected request selected by said selection means and obtaining a processed image; and
   output means for outputting a plurality of images processed by said processing means in a predetermined order regardless of an order in which said processing means has processed the plurality of images.

38. A computer-readable storage medium storing a program for executing an examination method, the method comprising the steps of:
   inputting examination request information including a plurality of examination methods arranged in an order for a patient;
   changing the order into a changed order;
   performing examination in accordance with the changed order and obtaining results therefrom; and
   outputting the obtained results of the plurality of examination methods, in a predetermined order regardless of the changed order.

39. A computer-readable storage medium storing a program for executing an examination method, the method comprising the steps of:
   inputting examination request information including a plurality of examination methods arranged in an order for a patient;
   handling each of the plurality of examination methods as an examination method object and attaching a status to each of the examination method objects;
   displaying the examination method objects of the plurality of examination methods;
   changing a display format of each of the examination method objects according to the status;
   selecting one of the examination method objects;
   performing examination in accordance with an examination condition determined by the selected examination method object and in accordance with an examination mode determined by the status of the selected examination method object; and
   outputting a plurality of examined examination method objects in the order in the examination request information regardless of an order in which the plurality of examination methods have been performed.

40. A computer-readable storage medium storing a program for executing an examination method, the method comprising the steps of:

inputting examination request information including a plurality of examination methods arranged in an order for a patient;

handling each of the plurality of examination methods as an examination method object and attaching a status to each of the examination method objects;

displaying the examination method objects of the plurality of examination methods;

changing a display format of each of the examination method objects according to the status;

changing the order into a changed order;

performing examination in accordance with an examination condition determined by the examination method object selected on the basis of the changed order and in accordance with an examination mode determined by the status of the selected examination method object; and outputting a plurality of examined examination method objects in the order in the examination request information regardless of the changed order.

41. A computer-readable storage medium storing a program for executing a radiographic method of obtaining a radiograph of an object, the method comprising the steps of:

inputting radiographic request information including a plurality of radiographic requests for a patient;

performing radiography in accordance with the input radiographic request information and obtaining a radiograph, wherein an order in which radiography for the plurality of radiographic requests is performed is changeable; and outputting the obtained radiographs of the plurality of radiographic requests, in a predetermined order regardless of an order in which the radiography has been performed for the plurality of radiographic requests.

42. A computer-readable storage medium storing a program for executing an examination method, the method comprising the steps of:

inputting examination request information including a plurality of examination methods for a patient;

selecting one from the plurality of examination methods, wherein an order in which one from the plurality of examination methods is selected is changeable;

performing the selected examination method and obtaining a result therefrom; and outputting the results of the plurality of examination methods in a predetermined order regardless of an order in which the plurality of examination methods have been performed.

\* \* \* \* \*

UNITED STATES PATENT AND TRADEMARK OFFICE
CERTIFICATE OF CORRECTION

PATENT NO. : 6,501,827 B1
DATED : December 31, 2002
INVENTOR(S) : Toru Takasawa

It is certified that error appears in the above-identified patent and that said Letters Patent is hereby corrected as shown below:

Column 1,
Line 13, "therefore." should read -- therefor. --.

Column 4,
Line 1, "fronts"→" should read -- front"→ --.

Column 6,
Line 57, "110" should read -- 110. --.

Column 8,
Line 21, "fronts"" should read -- front" --.

Column 9,
Line 19, "In" should read -- in --.
Line 29, "Information." should read -- information. --.
Line 50, "states"" should read -- state" --.

Column 10,
Line 28, "5)" should read -- 5). --.

Column 11,
Line 6, "stop" should read -- step --.

Signed and Sealed this

Twenty-first Day of October, 2003

JAMES E. ROGAN
*Director of the United States Patent and Trademark Office*